(12) United States Patent
Sethna et al.

(10) Patent No.: US 10,219,891 B2
(45) Date of Patent: Mar. 5, 2019

(54) STENT-GRAFT PROSTHESES HAVING A STITCH PATH THAT PERMITS RELATIVE MOVEMENT BETWEEN A STENT AND A TUBULAR GRAFT

(71) Applicant: Medtronic Vascular, Inc., Santa Rosa, CA (US)

(72) Inventors: Sohrab Sethna, Santa Rosa, CA (US); Ana Zavala, Santa Rosa, CA (US)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 146 days.

(21) Appl. No.: 14/624,631

(22) Filed: Feb. 18, 2015

(65) Prior Publication Data

US 2016/0235517 A1 Aug. 18, 2016

(51) Int. Cl.
*A61F 2/07* (2013.01)
*A61F 2/89* (2013.01)

(52) U.S. Cl.
CPC .................. *A61F 2/07* (2013.01); *A61F 2/89* (2013.01); *A61F 2002/075* (2013.01); *A61F 2230/0054* (2013.01)

(58) Field of Classification Search
CPC ......... A61F 2/07; A61F 2002/075; A61F 2/89
See application file for complete search history.

(56) References Cited

U.S. PATENT DOCUMENTS

| | | | |
|---|---|---|---|
| 5,824,037 A * | 10/1998 | Fogarty | A61F 2/07 623/1.13 |
| 6,042,605 A | 3/2000 | Martin et al. | |
| 6,245,099 B1 | 6/2001 | Edwin et al. | |
| 7,232,459 B2 * | 6/2007 | Greenberg | A61F 2/07 623/1.13 |
| 8,034,096 B2 | 10/2011 | Hunt | |

\* cited by examiner

*Primary Examiner* — Christopher D. Prone
(74) *Attorney, Agent, or Firm* — Medler Ferro Woodhouse & Mills PLLC

(57) ABSTRACT

A stent-graft prosthesis includes a tubular graft and a stent coupled to the tubular graft via a plurality of stitches. The stent has a sinusoidal pattern defined by a plurality of crowns and a plurality of struts. The stitches form a stitch path having a sinusoidal pattern that corresponds to the sinusoidal pattern of the stent. A width of curved segments of the stitch path that are disposed over crowns of the stent is configured to permit relative longitudinal movement between the stents and the tubular graft. A width of intermediate segments of the stitch path that are disposed over struts of the stent may be configured to restrict or permit relative circumferential movement between the stents and the tubular graft. The stitch path may include a plurality of transverse stitches in order to prevent exposure of the crowns beyond the stitch path.

10 Claims, 8 Drawing Sheets

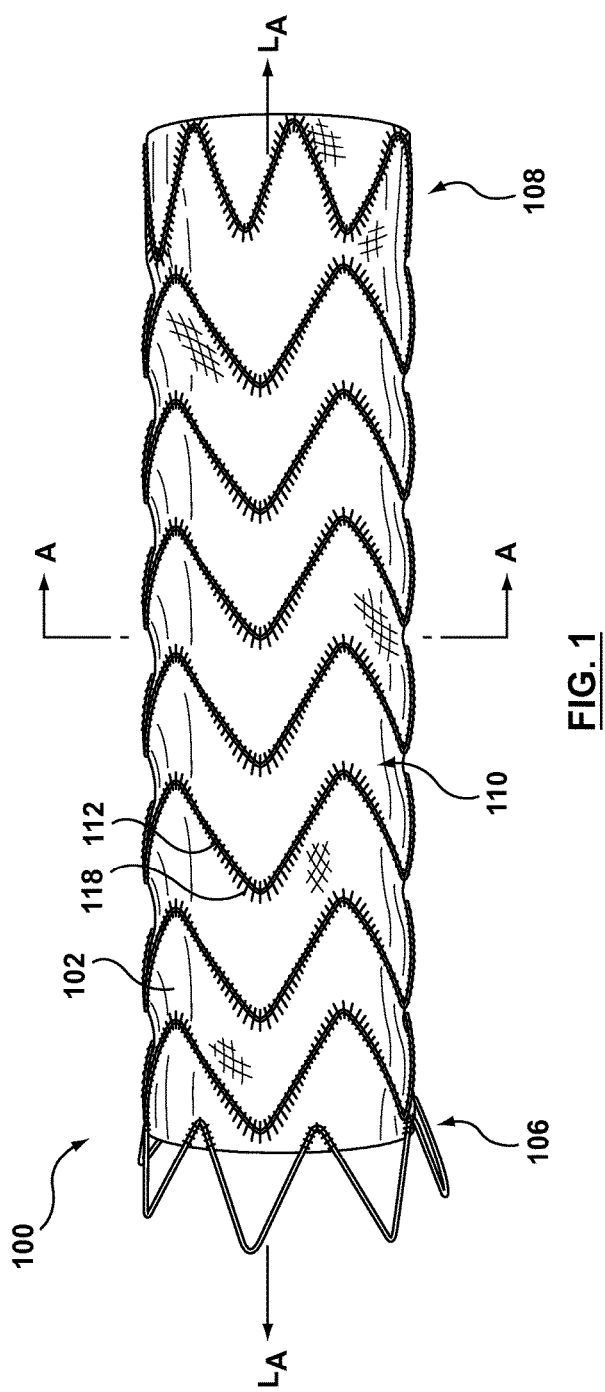
FIG. 1
FIG. 1A
FIG. 1B

STENT-GRAFT PROSTHESES HAVING A STITCH PATH THAT PERMITS RELATIVE MOVEMENT BETWEEN A STENT AND A TUBULAR GRAFT

FIELD OF THE INVENTION

The invention relates in general to stent-graft prostheses, and more particularly to a stitch path that permits relative movement between a stent and a tubular graft.

BACKGROUND OF THE INVENTION

Prostheses for implantation in blood vessels or other similar organs of the living body are, in general, well known in the medical art. For example, prosthetic endovascular grafts constructed of biocompatible materials have been employed to replace or bypass damaged or occluded natural blood vessels. In general, endovascular grafts include a graft anchoring component that operates to hold a tubular graft component of a suitable graft material in its intended position within the blood vessel. Most commonly, the graft anchoring component is one or more radially compressible stents that are radially expanded in situ to anchor the tubular graft component to the wall of a blood vessel or anatomical conduit. In addition, the stents also have a patency function in that the stents keep the graft open and radially expanded along portions of the graft that are not necessarily opposed to the vessel wall, i.e., along portions of graft disposed within an aneurysm sac. Thus, endovascular grafts are typically held in place by mechanical engagement and friction due to the apposition forces provided by the radially expanded stents.

Grafting procedures are also known for treating aneurysms. Aneurysms result from weak, thinned blood vessel walls that "balloon" or expand due to aging, disease and/or blood pressure in the vessel. Consequently, aneurysmal vessels have a potential to rupture, causing internal bleeding and potentially life threatening conditions. Grafts are often used to isolate aneurysms or other blood vessel abnormalities from normal blood pressure, reducing pressure on the weakened vessel wall and reducing the chance of vessel rupture. As such, a tubular endovascular graft may be placed within the aneurysmal blood vessel to create a new flow path and an artificial flow conduit through the aneurysm, thereby reducing if not nearly eliminating the exertion of blood pressure on the aneurysm.

In general, rather than performing an open surgical procedure to implant a bypass graft that may be traumatic and invasive, endovascular grafts which may be referred to as stent-grafts are preferably deployed through a less invasive intraluminal delivery procedure. More particularly, a lumen or vasculature is accessed percutaneously at a convenient and less traumatic entry point, and the stent-graft is routed through the vasculature to the site where the prosthesis is to be deployed. Intraluminal deployment is typically effected using a delivery catheter with coaxial inner and outer tubes or shafts arranged for relative axial movement. For example, a self-expanding stent-graft may be compressed and disposed within a distal end of an outer shaft or sheath component of the delivery catheter distal of a stop fixed to an inner shaft or member. The delivery catheter is then maneuvered, typically tracked through a body lumen until a distal end of the delivery catheter and the stent-graft are positioned at the intended treatment site. The stop on the inner member is then held stationary while the sheath component of the delivery catheter is withdrawn. The stop on the inner member prevents the stent-graft from being withdrawn with the sheath component. As the sheath component is withdrawn, the stent-graft is released from the confines thereof and radially self-expands so that at least a portion of it contacts and substantially conforms to a portion of the surrounding interior of the lumen, e.g., the blood vessel wall or anatomical conduit.

In some applications, the blood vessel wall or anatomical conduit in which the stent-graft is to be implanted is highly curved or angled. There is a need in the art for improved stent-grafts that are kink-resistant in order to substantially conform to highly curved or angled anatomy. Improved flexibility and patency results in improved hemodynamic blood flow through highly angulated stent grafts.

BRIEF SUMMARY OF THE INVENTION

A stent-graft prosthesis includes a tubular graft defining a lumen there-through and having a first end and an opposing second end with a body extending there-between. A stent is coupled to the body of the tubular graft. The stent has a sinusoidal pattern defined by a plurality of crowns and a plurality of struts with each crown being formed between a pair of opposing struts. A plurality of stitches couples the stent to the body of the tubular graft. The plurality of stitches form a stitch path having a sinusoidal pattern that corresponds to the sinusoidal pattern of the stent. A width of each of first and second curved segments of the stitch path that are disposed over respective first and second crowns of a pair of opposing crowns of the stent is greater than a width of the respective first or second crown of the pair of opposing crowns so as to permit relative longitudinal movement between the pair of opposing crowns and the tubular graft. The stent-graft prosthesis has a compressed configuration for delivery within a vasculature and an expanded configuration for deployment within a body lumen.

A stent-graft prosthesis includes a tubular graft defining a lumen there-through and having a first end and an opposing second end with a body extending there-between. A stent is coupled to the body of the tubular graft. The stent is a ring having a sinusoidal pattern defined by a plurality of crowns and a plurality of struts with each crown being formed between a pair of opposing struts. A plurality of stitches couples the stent to the body of the tubular graft. The plurality of stitches form a stitch path having a sinusoidal pattern that corresponds to the sinusoidal pattern of the stent. A width of the stitch path varies such that a width of each of first and second curved segments of the stitch path that are disposed over respective first and second crowns of a pair of opposing crowns of the stent is greater than a width of the respective first or second crown of the pair of opposing crowns and a width of a third intermediate segment of the stitch path disposed over a strut of the plurality of struts that extends between the first and second crowns of the pair of opposing crowns is approximately the same as a width of the strut so as to permit relative longitudinal movement between the pair of opposing crowns and the tubular graft and prevent relative circumferential movement between the pair of opposing crowns and the tubular graft. The stent-graft prosthesis has a compressed configuration for delivery within a vasculature and an expanded configuration for deployment within a body lumen.

A stent-graft prosthesis includes a tubular graft defining a lumen there-through and having a first end and an opposing second end with a body extending there-between. A stent is coupled to the body of the tubular graft. The stent has a sinusoidal pattern defined by a plurality of crowns and a plurality of struts with each crown being formed between a pair of opposing struts. A plurality of stitches couples the stent to the body of the tubular graft. The plurality of stitches form a stitch path that corresponds to at least a portion of the sinusoidal patterned stent. A width of a first curved segment of the stitch path that is disposed over a first crown of the stent is greater than a width of the first crown of the stent so as to permit relative longitudinal movement between the first crown and the tubular graft. A plurality of transverse stitches extend between the plurality of stitches disposed over the first crown, the transverse stitches being configured to prevent the first crown from extending beyond the stitch path. The stent-graft prosthesis has a compressed configuration for delivery within a vasculature and an expanded configuration for deployment within a body lumen.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a side view of a stent-graft prosthesis according to an embodiment hereof, the stent-graft prosthesis including a stitch path that is configured to permit relative longitudinal movement between a plurality of stents and a tubular graft via wider curved segments of the stitch path which are disposed over crowns of the stents and is also configured to restrict or prevent relative circumferential movement between the stents and the tubular graft via narrower intermediate segments of the stitch path which are disposed over struts of the stents, wherein the stent-graft prosthesis is shown in its expanded or deployed configuration.

FIG. 1A is a cross-sectional view taken along line A-A of FIG. 1.

FIG. 1B is an end view of the stent-graft prosthesis of FIG. 1, wherein the stent-graft prosthesis is shown in its radially compressed or delivery configuration.

DETAILED DESCRIPTION OF THE INVENTION

Figure 2:
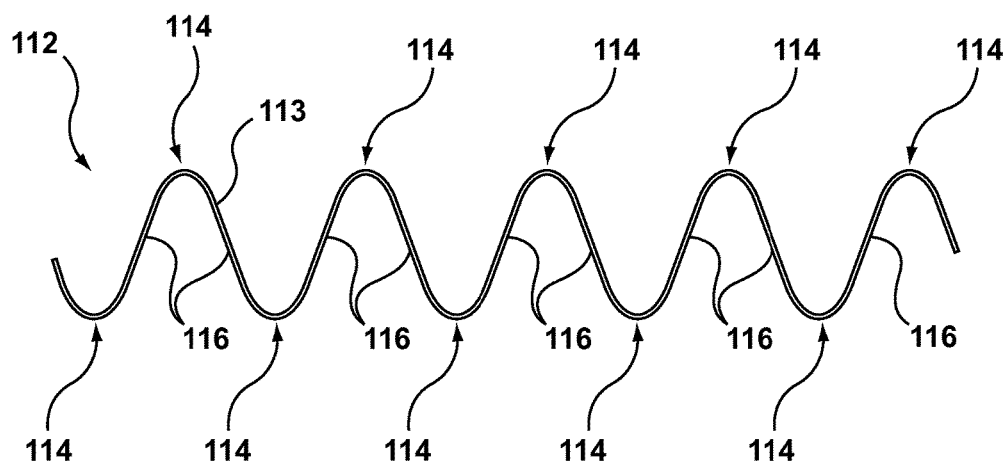
FIG. 2 is an illustration of a stent of the stent-graft prosthesis of FIG. 1, wherein the stent is removed from the stent-graft and laid flat for illustrative purposes only.

Specific embodiments are now described with reference to the figures, wherein like reference numbers indicate identical or functionally similar elements. Unless otherwise indicated, the terms "proximal" refers to the portion a stent-graft nearer the heart by way of blood flow path while "distal" refers the portion of a stent-graft further from the heart by way of blood flow path. In addition, the term "self-expanding" is used in the following description with reference to one or more stent structures of the prostheses hereof and is intended to convey that the structures are shaped or formed from a material that can be placed in a compressed or constricted delivery configuration and allowed to expand into a deployed configuration. Non-exhaustive exemplary self-expanding materials include stainless steel, a pseudo-elastic metal such as a nickel titanium alloy or nitinol, various polymers, or a so-called super alloy, which may have a base metal of nickel, cobalt, chromium, or other metal. Various polymers that can be made to have "self-expanding" characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other "self-expanding" polymers.

The following detailed description is merely exemplary in nature and is not intended to limit the invention or the application and uses of the invention. Although the description of the invention is in the context of treatment of blood vessels such as the aorta, the invention may also be used in any other body passageways where it is deemed useful. Furthermore, there is no intention to be bound by any expressed or implied theory presented in the preceding technical field, background, brief summary or the following detailed description.

Embodiments hereof relate to stent-graft prostheses having a stitch pattern or path that permits relative movement between a stent and a tubular graft of a stent-graft prosthesis. More particularly, stitch paths described herein for coupling a stent to the tubular graft permit relative longitudinal movement or sliding between the stent and tubular graft in order to avoid kinking of the tubular graft when the stent-graft prosthesis is implanted within highly curved or angled anatomy. The stitch paths include wider stitches around select crowns on the stent so that the crowns are not rigidly constrained onto the tubular stent graft but rather are allowed to slide or shift in a longitudinal direction when the stent-graft prosthesis is bent or curved during implantation. Further, in some embodiments hereof, stitch paths described herein for coupling a stent to the tubular graft also permit relative circumferential movement between the stent and tubular graft in order to provide the stent-graft with maximum flexibility. In addition to kink resistant and increased flexibility and patency properties, stitch paths described herein also improve the recoil ability of the stent-graft prosthesis because the wider stitches around select crowns on the stent reduce the possibility of the stent being caught in the stitching during the recoil process. Further, stitch paths described herein also reduce fatigue of the stent-graft prosthesis because the wider stitches around select crowns on the stent reduce the possibility of the stent being trapped by, caught on, or otherwise interfering with an adjacent stent and bowing as a result when implanted within a highly curved or angled anatomy.

More particularly, FIG. 1 is a side view of stent-graft prosthesis 100 in its expanded or deployed configuration. FIG. 1A is a cross-sectional view of stent-graft prosthesis 100 taken along line A-A of FIG. 1, while FIG. 1B is an end view of stent-graft prosthesis 100 in its radially compressed or delivery configuration. Stent-graft prosthesis 100 includes a tubular graft 102 having a longitudinal axis $L_A$, a first edge or end 106, a second edge or end 108, and a body 110 there-between which defines a lumen 104 through stent-graft prosthesis 100. In an embodiment, first end 106 of tubular graft 102 may be referred to as a proximal end or edge of tubular graft 102 and a proximal end or edge of stent-graft prosthesis 100, which is conventionally the end that is coupled to a tip capture mechanism of a delivery system, and second end 108 of tubular graft 102 may be referred to as a distal end or edge of graft 108 and a distal end or edge of stent-graft prosthesis 100. Tubular graft 102 is formed from a synthetic fabric material, for example and not limited to, a low-porosity woven or knit polyester, PET (polyethylene terephthalate) or DACRON, or other suitable materials. In another embodiment, the graft material could also be a polymeric material such as but not limited to nylon, polyester, PTFE, ePTFE, polypropylene and silicone or the graft material could also be a natural material such as pericardium or another membranous tissue such as intestinal submucosa.

Figure 3:
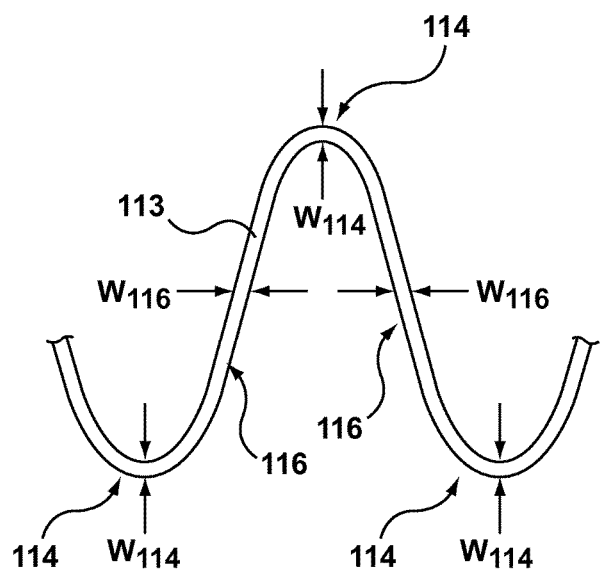
FIG. 3 is an enlarged view of a portion of the stent of FIG. 2.

Stent-graft prosthesis 100 also includes at least one radially-compressible stent or scaffold 112 that is coupled to body 110 of tubular graft 102 for supporting the graft material and is operable to self-expand into apposition with an interior wall of a body vessel (not shown) and is operable to expand to its designed diameter to aid in blood flow through the stent graft. In the embodiment depicted in FIG. 1, stent-graft prosthesis 100 is shown in its fully expanded or deployed configuration and includes a series of nine independent or separate cylindrical stents 112. Each stent 112 is constructed from a self-expanding or spring material, such as Nitinol. As best shown in FIG. 2, each stent 112 is a wire or strand 113 shaped or formed into a sinusoidal patterned ring including a plurality of crowns or bends 114 and a plurality of struts or straight segments 116 with each crown being formed between a pair of opposing struts. Stents 112 are shown in FIG. 1 as having identical sinusoidal patterns but it will be understood by one of ordinary skill in the art that one or more of stents 112 may have a different pattern or configuration. FIG. 2 illustrates a stent 112 removed from stent-graft 100 and laid flat for illustrative purposes only. As best shown on FIG. 3, which is an enlarged view of a portion of a stent 112, in an embodiment hereof, wire 113 which forms stent 112 has a consistent or non-varying width. More particularly, struts 116 of stent 112 have a width $W_{116}$ while crowns 114 of stent 112 have a width $W_{114}$. Width $W_{116}$ is equal to or the same as width $W_{114}$. As used herein, width $W_{114}$ of crowns 114 as well as width $W_{116}$ of struts 116 refers to the width of wire 113 of stent 112. However, in another embodiment hereof (not shown), the wire which forms the stent may have a non-consistent or varying width in which the struts of the stent are narrower or wider than the crowns of the stent.

For description purposes only, the stent that is coupled adjacent and proximate to first end 106 of tubular graft 102 is referred to herein as first or proximal end stent and the stent that is coupled adjacent and proximate to second end 108 of tubular graft 102 is referred to herein as second or distal end stent. In the embodiment of FIG. 1, the proximal end stent has endmost crowns that extend beyond first or proximal end 106 of tubular graft 102 in an open web or free-flow configuration while the distal end stent has endmost crowns that are covered or lined by tubular graft 102 and do not extend past or beyond second or distal end 108 of tubular graft 102 in a closed web configuration. In another embodiment hereof (not shown), the proximal end stent has endmost crowns that are covered or lined by tubular graft 102 and do not extend past or beyond first or proximal end 106 of tubular graft 102 in a closed web configuration and/or the distal end stent has endmost crowns that extend beyond second or distal end 108 of tubular graft 102 in an open web or free-flow configuration.

Although stent-graft 100 is shown with nine stents in FIG. 1, it will be understood by one of ordinary skill in the art that stent-graft prosthesis 100 may include a greater or smaller number of stents depending upon the desired length of stent-graft prosthesis 100 and/or the intended application thereof. Further, in the embodiment shown in FIG. 1, stents 112 are coupled to an outside surface of tubular graft 102. However, stents 112 may alternatively be coupled to an inside surface of tubular graft 102. When stent-graft prosthesis 100 is used for treating an aneurysm, stents 112 have sufficient radial spring force and flexibility to conformingly engage stent-graft prosthesis 100 with the body lumen inner wall, to avoid excessive leakage, and prevent pressurization of the aneurysm, i.e., to provide a leak-resistant seal. Although some leakage of blood or other body fluid may occur into the aneurysm isolated by stent-graft prosthesis 100, an optimal seal will reduce the chances of aneurysm pressurization and resulting rupture. In addition to the sealing aspect, stents 112 have sufficient radial spring force to maintain patency of stent-graft prosthesis 100 in order to allow for unobstructed blood flow there-through.

Stents 112 are coupled to tubular graft 102 by a plurality of stitches 118. More particularly, stitches 118 form a stitch path 120 having a sinusoidal pattern that corresponds to the sinusoidal pattern of stent 112. Stitch path 120 is shown removed from stent-graft 100 and laid flat for illustrative purposes in FIG. 4. As used herein, "a plurality of stitches" refers to a plurality of individual sutures or filaments or a single elongated suture or filament that forms a plurality of stitches. The sinusoidal pattern of stitch path 120 includes a plurality of curved segments 122 and a plurality of intermediate segments 124 with each curved segment being formed between a pair of opposing intermediate segments. Stitches 118 extend over and conform to the outer surface of stents 112 so that stents 112 are held flush against the outer surface of tubular graft 102. Stated another way, stitches 118 extend over and conform to the outer surface of stents 112 so that stents 112 are held in the sewing plane.

Figure 4:
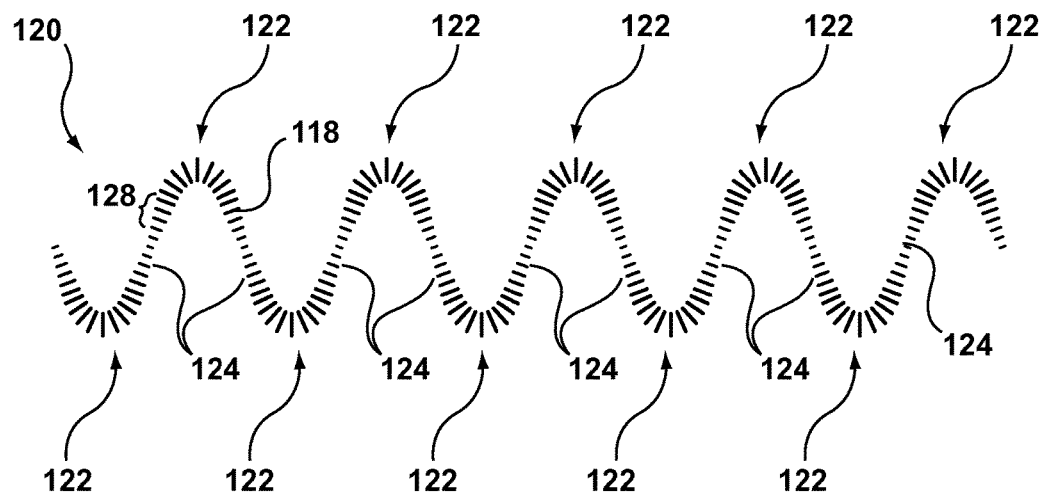
FIG. 4 is an illustration of the stitch path for a stent of the stent-graft prosthesis of FIG. 1, wherein the stitch path is removed from the stent-graft and laid flat for illustrative purposes only.
Figure 5:
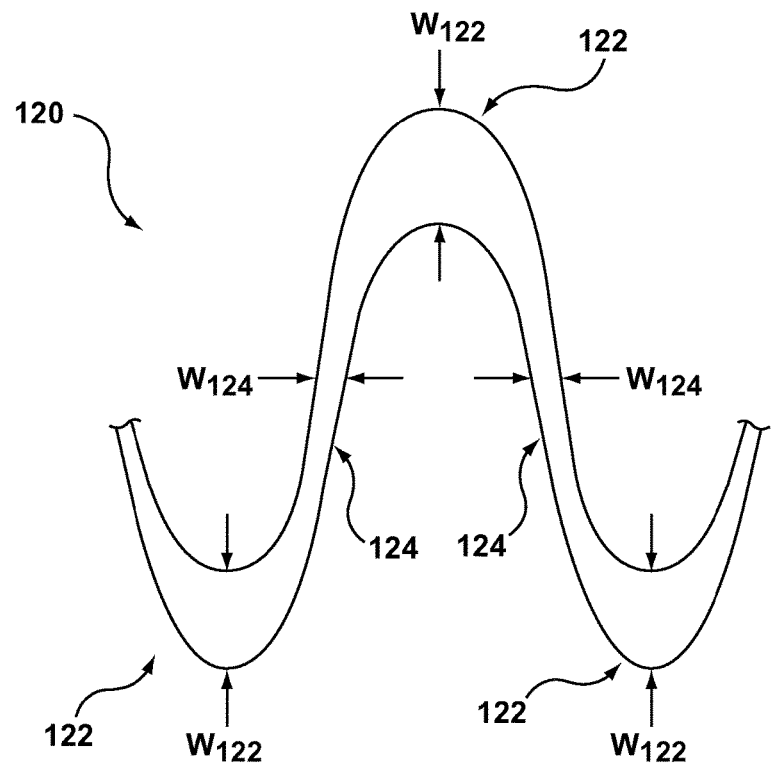
FIG. 5 is an enlarged view of a portion of the stitch path of FIG. 4, wherein an outline of the stitch path is shown to illustrate the shape thereof while the stitches are removed for sake of clarity.

As best shown on FIG. 5, which is an enlarged view of a portion of FIG. 4, stitches 118 which form stitch path 120 have a varying or non-consistent width. More particularly, curved segments 122 of stitch path 120 have a width $W_{122}$ configured to permit relative longitudinal movement between the stent and the tubular graft and intermediate segments 124 of stitch path 120 have a width $W_{124}$ configured to restrict or prevent relative circumferential movement between the stent and the tubular graft. As used herein, width $W_{122}$ of curved segments 122 refers to the width of stitches 118 within or along a curved segment of stitch path 120. As shown in FIG. 5, the width of stitches 118 within transition zones 128 that extend between curved segments 122 of stitch path 120 and intermediate segments 124 of stitch path 120 gradually or continuously taper or decrease from the wider width of curved segments 122 (i.e., width $W_{122}$) to the narrower width of intermediate segments 124 (i.e., width $W_{124}$).

The width $W_{122}$ of curved segments 122 of stitch path 120 is greater than the width $W_{114}$ of crowns 114 of stent 112 in order to allow relative longitudinal movement between crowns 114 and tubular graft 102. Stated another way, stitches 118 along curved segments 122 of stitch path 120 are wider than or open-spaced relative to crowns 114 of stent 112 so that crowns 114 of stent 112 are permitted to slide, shift, or otherwise move in a longitudinal direction within a pocket or compartment formed between crowns 114 and tubular graft 102. In an embodiment hereof, the width $W_{114}$ of crowns 114 of stent 112 is approximately 0.5 mm while the width $W_{122}$ of curved segments 122 ranges between 4.5 mm and 5.0 mm. However, it will be understood by one of ordinary skill in the art that the width $W_{114}$ of crowns 114 of stent 112 may vary according to application and design. In addition, the width $W_{122}$ of curved segments 122 may vary depending upon the amount of relative motion that is desired as well as the width $W_{114}$ of crowns 114 of stent 112.

Figure 6:
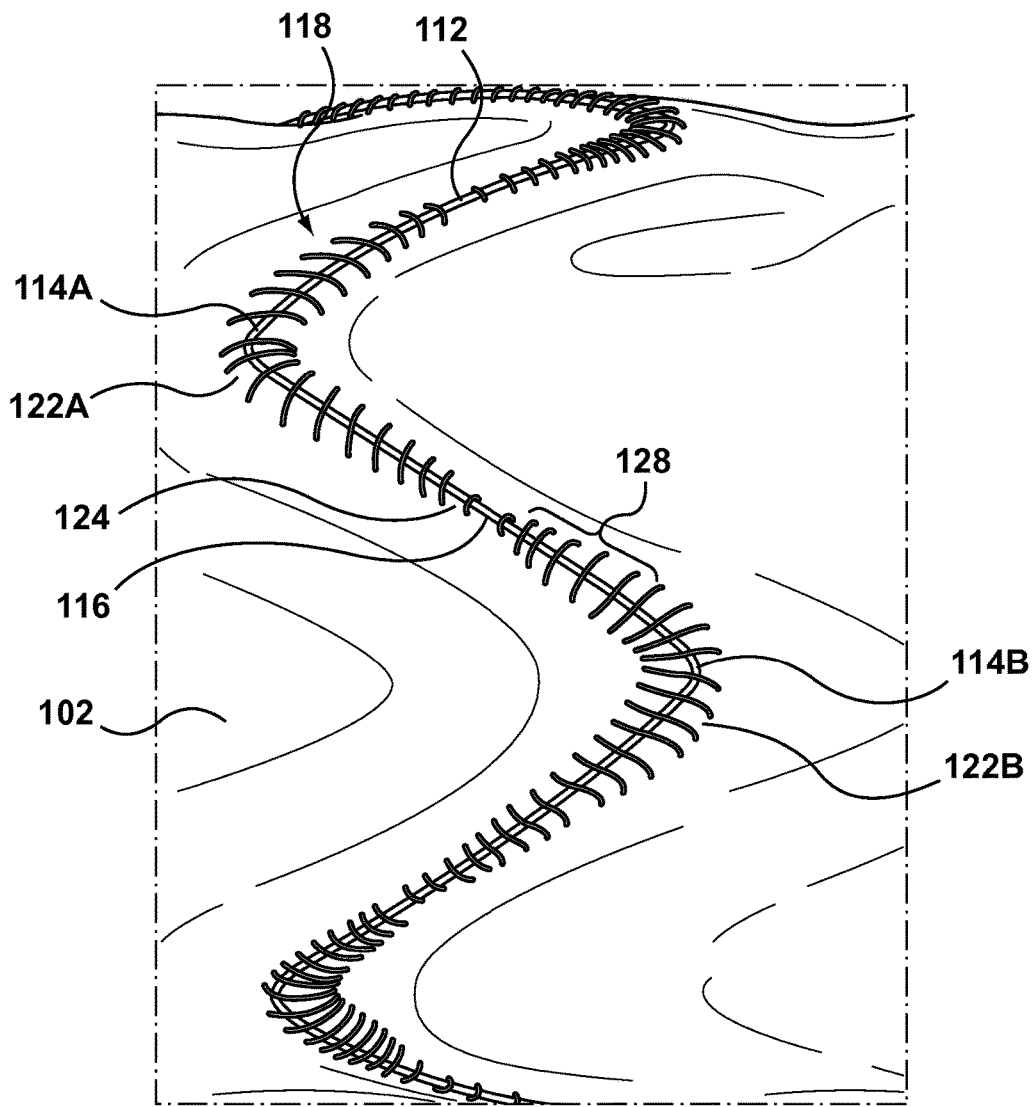
FIG. 6 is an enlarged view of a portion of the stent-graft prosthesis of FIG. 1.

For description purposes only, a crown 114 having a wider stitch path disposed thereover, i.e., having curved segments 122 of stitch path 120 disposed thereover, is referred to herein as a slidable crown because such crown is permitted to slide, shift, or otherwise move in a longitudinal direction within a pocket or compartment formed between crowns 114 and tubular graft 102. In an embodiment hereof, the slidable crowns of a stent 112 include at least a pair of opposing crowns. As used herein, a pair of opposing crowns includes two adjacent or consecutive crowns that are curved in opposing or opposite directions. More particularly, with reference to FIG. 6, a width of each of first and second curved segments 122A, 122B, respectively, of stitch path 120 that are disposed over respective first and second crowns 114A, 114B of a pair of opposing crowns of stent 112 is greater than a width of the respective first or second crown 114A, 114B of the pair of opposing crowns so as to permit relative longitudinal movement between first and second crowns 114A, 114B and tubular graft 102. In an embodiment hereof, as shown in FIG. 1, the slidable crowns of a stent 112 include all crowns of the stent. More particularly, a width of each curved segment 122 of stitch path 120 disposed over each crown 114 of stent 112 is greater than the width of each crown of stent 112. Stated another way, in one embodiment, every curved segment 122 of stitch path 120 is wider than its respective crown 114 of stent 112 such that every crown 114 of a stent 112 is permitted to longitudinally slide relative to tubular graft 102.

However, in another embodiment hereof, the slidable crowns of a stent 112 are strategically positioned in order to selectively increase the flexibility at select or particular locations along the stent-graft prosthesis. For example, as shown on FIG. 7, a stent-graft prosthesis 700 includes slidable crowns positioned along an inner longitudinal edge or curve 730 of the stent-graft prosthesis so that stent-graft prosthesis 700 is configured for implantation within an aortic arch anatomy having a similar curvature. Stent-graft prosthesis 700 is shown curved to simulate implantation within an aortic arch. More particularly, stent-graft prosthesis 700 includes a tubular graft 702 which is similar in structure to tubular graft 102 and a plurality of stents 712 which are similar in structure to stents 112. Stents 712 positioned along an mid portion of a body portion 710 of tubular graft 702 are herein referred to as stents 712A, 712B, 712C, 712D as shown on FIG. 7. Each of stents 712A, 712B, 712C, 712D includes at least a pair of opposing crowns that are slidable crowns, i.e., the stitches (not shown in the side view of FIG. 7) disposed over these crowns are wider than or open-spaced relative to the width of the crowns so that the crowns are permitted to slide, shift, or otherwise move in a longitudinal direction. The slidable crowns of each stent 712A, 712B, 712C, 712D are longitudinally aligned on stent-graft prosthesis 700 to be positioned along an inner longitudinal edge or curve 730 of the stent-graft prosthesis. As used herein, "longitudinally aligned" includes crowns that are aligned within a 15 degree angle relative to the circumference of the tubular graft. More particularly, in an embodiment, adjacent stents are positioned such that a slidable crown facing or oriented in a first direction of a first stent is aligned with a slidable crown facing or oriented in the first direction of a second stent (i.e., the slidable crowns of adjacent stents are in phase with each other). In another embodiment, adjacent stents are positioned such that a slidable crown facing or oriented a first direction of a first stent is aligned with a slidable crown facing or oriented a second or opposing direction of a second stent (i.e., the slidable crowns of adjacent stents are out of phase with each other).

Figure 7:
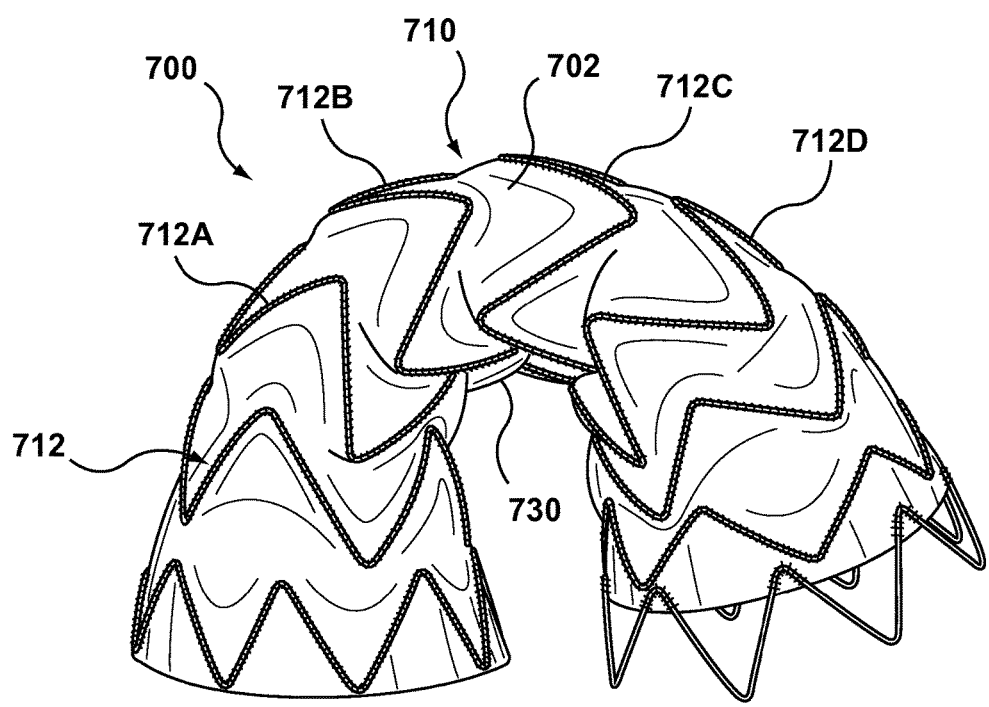
FIG. 7 is a side view of a stent-graft prosthesis according to another embodiment hereof, the stent-graft prosthesis including a plurality of slidable crowns positioned along an inner longitudinal edge of the stent-graft prosthesis, wherein the stent-graft prosthesis is shown in its expanded or deployed configuration and is shown curved to simulate implantation within an aortic arch.

The remaining crowns of each stent 712A, 712B, 712C, 712D are not slidable crowns but rather are tightly constrained to tubular graft 702. For example, the remaining crowns of each stent 712A, 712B, 712C, 712D are coupled to tubular graft 702 with stitching that has a width that is approximately the same as the width of the crown. As used herein, a stitch having "approximately" the same width as the width of the crown includes stitches that contact and abut against opposing edges of the crown such that relative longitudinal movement between the crown and the tubular graft is prevented. Stated another way, a stitch having approximately the same width as the width of the crown includes stitches that contact and abut against opposing edges of the crown such that no gap or space exists between the stitch and each edge of the crown. Although the embodiment of FIG. 7 depicts the slidable crowns selectively positioned along the inner longitudinal edge or curve of the prosthesis, it will be understood by those of ordinary skill in the art that the position of the slidable crowns on one or more stents of the stent-graft prosthesis may vary according to application and the slidable crowns may be positioned at any location on the prosthesis which is prone to kinking and thus require additional flexibility.

The width $W_{124}$ of intermediate segments 124 of stitch path 120 is approximately the same as the width $W_{116}$ of struts 116 of stent 112 in order to restrict or prevent circumferential movement between stent 112 and tubular graft 102. Stated another way, stitches 118 along intermediate segments 124 of stitch path 120 tightly constrain struts 116 of stent 112 to tubular graft 102 so that struts 116 of stent 112 are not permitted to slide, shift, or otherwise move in a circumferential direction. As used herein, a stitch having "approximately" the same width as the width of the strut includes stitches that contact and abut against opposing edges of the strut such that relative circumferential movement between the strut and the tubular graft is prevented. Stated another way, a stitch having "approximately" the same width as the width of the strut includes stitches that contact and abut against opposing edges of the strut such that no gap or space exists between the stitch and each edge of the strut. In an embodiment hereof, the width $W_{116}$ of struts 116 of stent 112 and thus also the width $W_{124}$ of intermediate segments 124 is approximately 0.5 mm. However, it will be understood by one of ordinary skill in the art that the width $W_{116}$ of struts 116 of stent 112 (and thus the corresponding width $W_{124}$ of intermediate segments 124) may vary according to application and design.

Thus, in the embodiment of FIGS. 1-6, stitch path 120 is configured to permit relative longitudinal movement between all stents 112 and tubular graft 102 via wider curved segments 122 of stitch path 120 that are disposed over crowns 114 of stents 112. Stitch path 120 is also configured to restrict or prevent relative circumferential movement between all stents 112 and tubular graft 102 via narrower intermediate segments 124 of stitch path 120 that tightly constrain struts 116 of stents 112 to the tubular graft. However, as described above with respect to FIG. 7, the slidable crowns of a stent 112 may be strategically positioned in order to selectively increase the flexibility at select or particular locations along the stent-graft prosthesis. Thus, not all crowns of a stent 112 are required to be slidable crowns and not all stents 112 of the stent-graft prosthesis are required to include slidable crowns. Each stent 112 of stent-graft prosthesis 100 may have a different configuration of slidable crowns configured to meet the flexibility requirements of a particular application.

Figure 8:
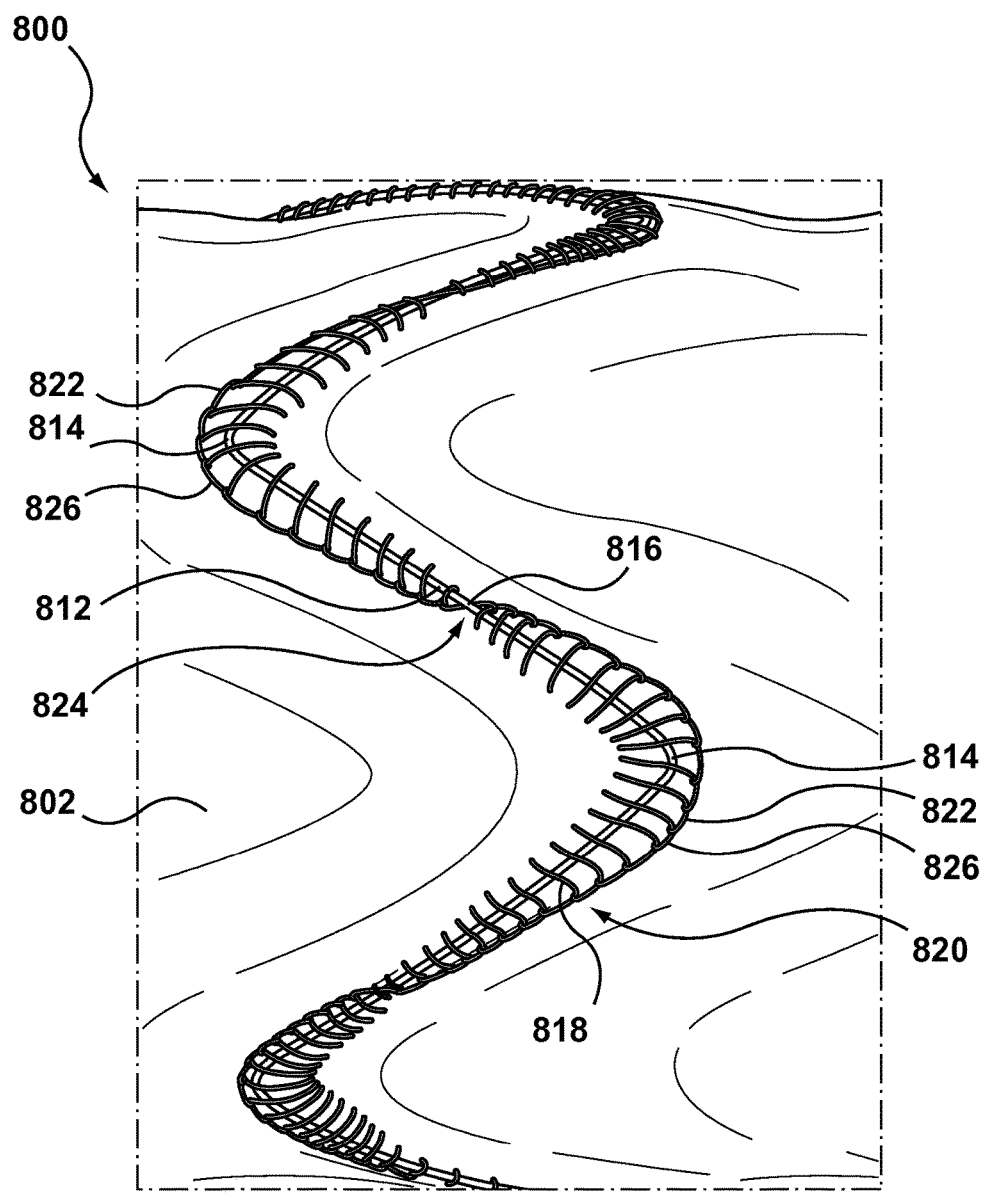
FIG. 8 is an enlarged view of a portion of stent-graft prosthesis according to another embodiment hereof, the stent-graft prosthesis including a stitch path that includes a plurality of transverse stitches in order to prevent exposure of the slidable crowns beyond the stitch path.

In an embodiment hereof, the stitch path may include a plurality of connection or transverse stitch along an outermost edge of each curved segment thereof in order to prevent exposure of the stent crown that is covered by the curved segment. Stated another way, the transverse stitches of the stitch path are configured to prevent each slidable crown from extending beyond the stitch path. More particularly, with reference to FIG. 8, a stent-graft prosthesis 800 includes a tubular graft 802 which is similar in structure to tubular graft 102 and a plurality of stents 812 which are similar in structure to stents 112. Similar to stitch path 120, stitches 818 of stitch path 820 are configured to permit relative longitudinal movement between all stents 812 and tubular graft 802 via wider curved segments 822 of stitch path 820 that are disposed over crowns 814 of stents 812. Stitches 818 of stitch path 820 are also configured to restrict or prevent relative circumferential movement between all stents 812 and tubular graft 802 via narrower intermediate segments 824 of stitch path 820 that tightly constrain struts 816 of stents 812 to the tubular graft. However, unlike stitch path 120, stitch path 820 includes a plurality of transverse stitches 826 that extend along an outermost edge of each curved segment 822 of stitch path 820 in order to prevent exposure of each crown 814 that is covered by the respective curved segment. Thus, as stents 812 move or slide longitudinally with respect to tubular graft 802, transverse stitches 826 prevent crowns 814 from extending beyond or past stitch path 820 and therefore prevent crowns 814 from inadvertently damaging or loosening stitches 818. While stitches 818 extend over a portion of stent 812, transverse stitches 826 extend parallel to a portion of stent 812 along an outermost edge of the stitch path. As used herein, outermost edge of each curved segment 822 refers to the edge of the stitch path which is disposed longitudinally beyond the apex or crown 814 in the direction of the respective apex or crown. Thus, since the direction of curvature of the apex or crowns 814 alternate due to the sinusoidal pattern of stent 812, the outermost edge of each curved segment 822 alternates in order to correspond with the alternating directions of crowns 814. Transverse stitches 826 and stitches 818 may be formed with a plurality of individual sutures or filaments or a single elongated suture or filament.

Figure 9:
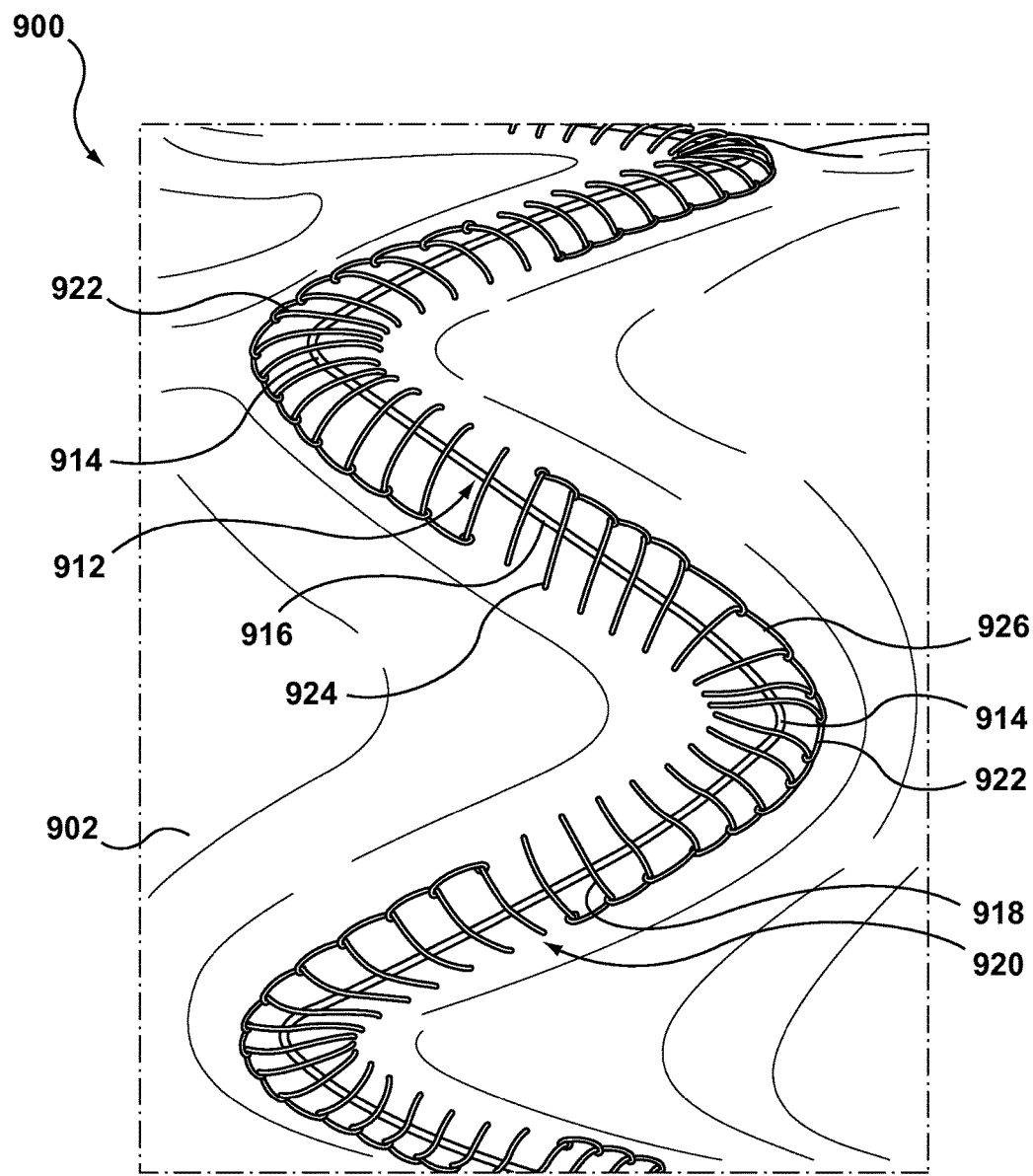
FIG. 9 is an enlarged view of a portion of stent-graft prosthesis according to another embodiment hereof, the stent-graft prosthesis including a stitch path that is configured to permit relative longitudinal movement between a plurality of stents and a tubular graft via wider curved segments disposed over crowns of the stents and is also configured to permit relative circumferential movement between the stents and the tubular graft via wider intermediate segments disposed over struts of the stents.

In another embodiment hereof, the stitch path may be configured to permit circumferential movement of one or more stents relative to the tubular graft. More particularly, with reference to FIG. 9, a stent-graft prosthesis 900 includes a tubular graft 902 which is similar in structure to tubular graft 902 and a plurality of stents 912 which are similar in structure to stents 112. Similar to stitch path 920, stitches 918 of stitch path 920 are configured to permit relative longitudinal movement between all stents 912 and tubular graft 902 via wider curved segments 922 of stitch path 920 that are disposed over crowns 914 of stents 912. However, unlike stitch path 120, stitches 918 of stitch path 920 are also configured to permit relative circumferential movement between all stents 912 and tubular graft 902 via wider intermediate segments 924 of stitch path 920 that are disposed over struts 916 of stents 912 to the tubular graft. The width of intermediate segments 924 of stitch path 920 is greater than the width of struts 916 of stent 912, thereby permitting relative circumferential movement of the stent relative to the tubular graft. Stated another way, stitches 918 along intermediate segments 924 of stitch path 920 are wider than or open-spaced relative to struts 916 of stent 912 so that struts 916 of stent 912 are permitted to slide, shift, or otherwise move in a circumferential direction within a pocket or compartment formed between struts 916 and tubular graft 902. In an embodiment hereof, stitch path 920 has a consistent or non-varying width such that the width of curved segments 922 of stitch path 920 is equal to the width of intermediate segments 924 of stitch path 920. Stitch path 920 may also include a plurality of transverse stitches 926 similar to transverse stitches 826 described above.

Figure 10:
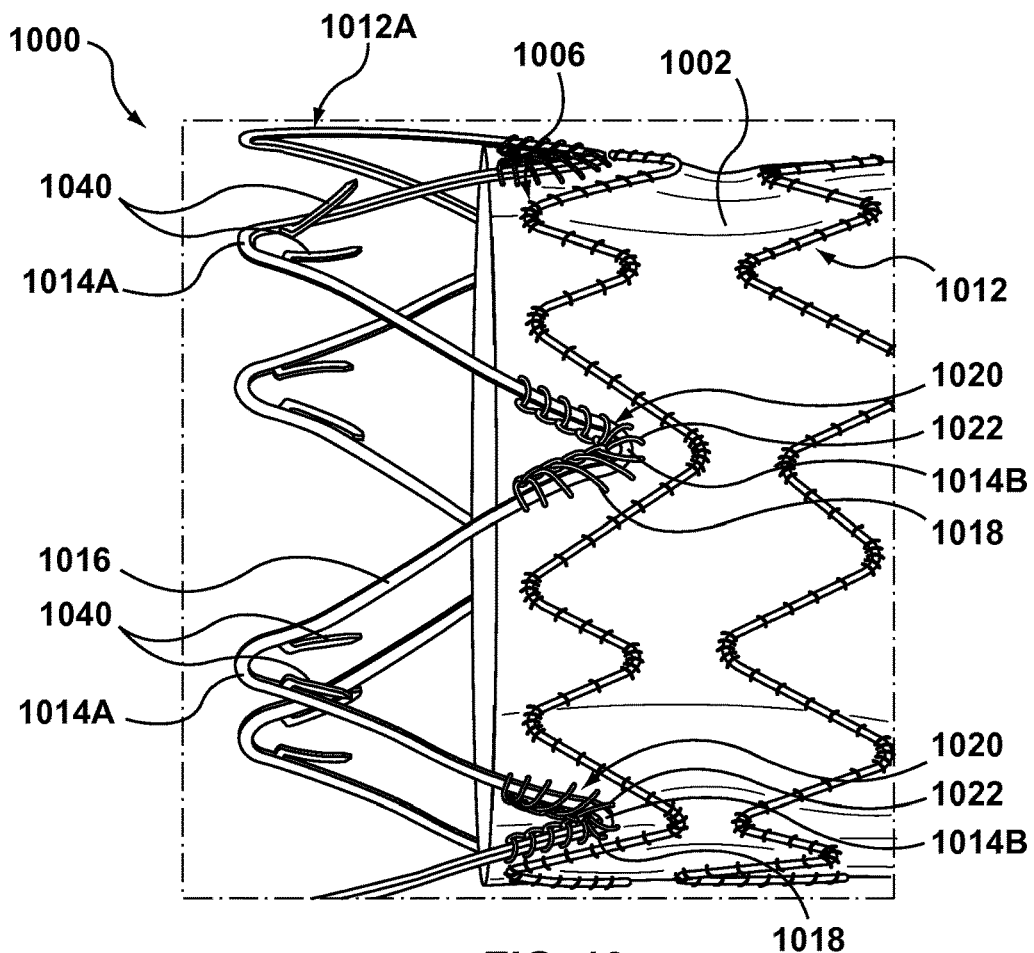
FIG. 10 is a side view of a first or proximal end of a stent-graft prosthesis according to another embodiment hereof, the stent-graft prosthesis including a stitch path which allows for relative movement between a first or proximal end stent and a tubular graft, wherein the stent-graft prosthesis is shown in its expanded or deployed configuration.
Figure 11:
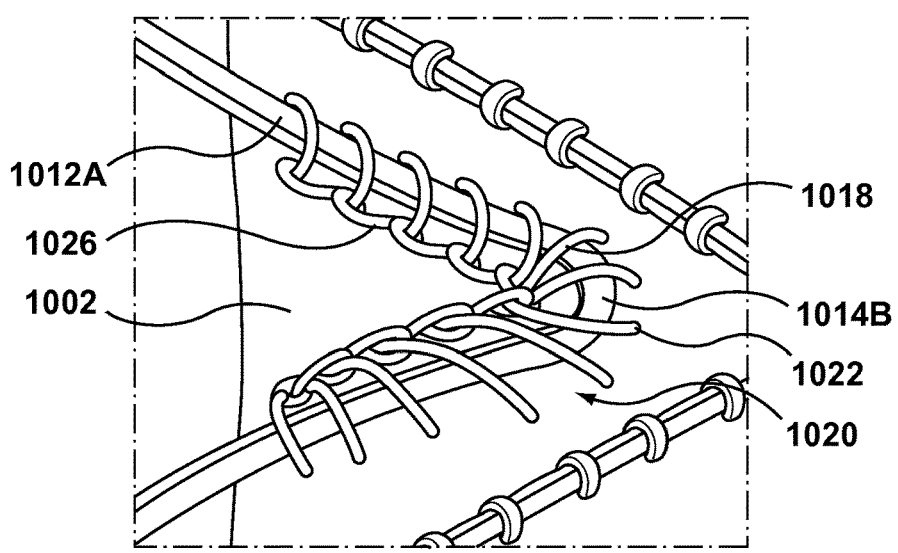
FIG. 11 is an enlarged view of a portion of the stent-graft prosthesis of FIG. 10.

FIGS. 10-11 illustrate another embodiment hereof in which a stitch path which allows for relative movement between a stent and a tubular graft is applied to the first or proximal end stent. As described above, the first or proximal end stent of a stent-graft prosthesis often has endmost crowns that extend beyond the first or proximal end of the tubular graft in an open web or free-flow configuration in order to couple the stent-graft prosthesis to a tip capture mechanism of a delivery system (not shown). As such, only a portion of the proximal end stent is coupled or attached to the tubular graft and the stitch path is modified to accommodate the open-web configuration of the proximal end stent.

More particularly, with reference to FIGS. 10-11, a stent-graft prosthesis 1000 includes a tubular graft 1002 which is similar in structure to tubular graft 102 and a plurality of stents 1012 which are similar in structure to stents 112. The proximal end stent is herein referred to as stent 1012A and includes a plurality of barbs 1040 at first or endmost crowns 1014A for anchoring stent-graft prosthesis 1000 into a vessel wall. The second or opposing crowns 1014B are disposed over and coupled to first or proximal end 1006 of tubular graft 1002. A plurality of stitches 1018 form a stitch path 1020 that corresponds to only a portion of the sinusoidal patterned stent 1012A that is coupled to tubular graft 1002. More particularly, stitch path 1020 includes only a plurality of curved segments 1022 disposed over second crowns 1014B of stent 1012A. The width of each curved segment 1022 of stitch path 1020 is greater than the width of crowns 1014B of stent 1012A in order to allow relative longitudinal movement between stent 1012A and tubular graft 1002. Stated another way, stitches 1018 along each curved segments 1022 of stitch path 1020 are wider than or open-spaced relative to crowns 1014B of stent 1012A so that crowns 1014B of stent 1012A are permitted to slide, shift, or otherwise move in a longitudinal direction within a pocket or compartment formed between crowns 1014B and tubular graft 1002. Stitch path 1020 also permits relative circumferential movement between stent 1012A and tubular graft 1002 since struts 1016 and endmost crowns 1014A of stent 1012A are not coupled to tubular graft 1002 and thus no stitching prevents or restricts such movement.

Stitch path 1020 may also include a plurality of transverse stitches 1026 similar to transverse stitches 826 described above. Unlike transverse stitches 826, however, transverse stitches 1026 are positioned or extend along an innermost edge of each curved segment 1022 of stitch path 1020. Since proximal end stent 1012A is often utilized to couple stent-graft prosthesis 1000 to a tip capture mechanism of a delivery system (not shown), proximal end stent 1012A is pulled towards first or proximal end 1006 of tubular graft 1002. Thus, in an embodiment hereof, transverse stitches 1026 are positioned or extend along an innermost edge of each curved segment 1022 of stitch path 1020 to secure proximal end stent 1012A to tubular graft 1002 when proximal end stent 1012A is coupled to and being pulled towards the tip capture mechanism of the delivery system and/or pulled by hemodynamic/blood flow forces. However, in another embodiment hereof, transverse stitches may additionally or alternatively be positioned along an outermost edge of each curved segment of the stitch path depending on the design and requirements of the stent graft prosthesis.

In any embodiment hereof, the relative longitudinal and/or circumferential movement between the stent(s) and tubular graft permitted by the stitch path may result in increased wear on the stitches thereof. Thus, the material of the stitches and/or the density of stitches may be varied in order to compensate for the permitted relative motion. For example, the stitches may be formed from a durable material such as but not limited to Ultra-high-molecular-weight polyethylene or DYNEEMA. In another example, the density of the stitches may be increased along a portion of the stitch path, i.e., curved segments of the stitch path that are disposed over slidable crowns, in order to compensate for the permitted relative motion. Each curved segment of the stitch path that is disposed over a slidable crown may, for example, include between 5 and 14 stitches per centimeter.

In any embodiment hereof, the stent(s) may be balloon-expandable rather than self-expanding as will be understood by one of ordinary skill in the art. In addition, rather than including a plurality of ring or annular stent(s) longitudinally spaced along a tubular graft, any embodiment hereof may include one or more helical stent(s) that coil or wind around an outer surface of a tubular graft. Similar to the ring or annular stent(s) described above, the helical stent(s) has a sinusoidal pattern defined by a plurality of crowns and a plurality of struts with each crown being formed between a pair of opposing struts and the stitch path utilized to couple the helical stent(s) to the tubular graft may selectively permit relative longitudinal and/or circumferential movement between a pair of opposing crowns and the tubular graft.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A stent-graft prosthesis comprising:
    a tubular graft defining a lumen there-through and having a first end and an opposing second end with a body extending there-between;
    a stent coupled to the body of the tubular graft, wherein the stent includes a plurality of curved crowns and a plurality of struts with each curved crown being formed between a pair of opposing struts such that the pluralities of curved crowns and struts collectively have a sinusoidal shape; and
    a plurality of stitches for coupling the stent to the body of the tubular graft, the plurality of stitches forming a stitch path that includes a plurality of curved segments defined by stitches of the plurality of stitches and a plurality of intermediate segments defined by stitches of the plurality of stitches, the pluralities of curved segments and intermediate segments collectively having a sinusoidal shape that corresponds to the sinusoidal shape of the pluralities of struts and curved crowns of the stent, wherein a width of the stitches that define each of first and second curved segments of the stitch path that are disposed over respective first and second curved crowns of a pair of opposing curved crowns of the stent is greater than a width of the respective first or second curved crown of the pair of opposing curved crowns so as to permit relative longitudinal movement between the pair of opposing curved crowns and the tubular graft, and
    wherein a width of the stitches that define an intermediate segment of the stitch path disposed over a strut of the plurality of struts that extends between the first and second curved crowns of the pair of opposing curved crowns is approximately the same as a width of the strut so as to prevent relative circumferential movement between the pair of opposing curved crowns and the tubular graft, and
    wherein the stitch path includes a first transition zone defined by stitches of the plurality of stitches and extending between the first curved segment of the stitch path and the intermediate segment of the stitch path disposed over the strut that extends between the first and second curved crowns of the pair of opposing curved crowns and a second transition zone defined by stitches of the plurality of stitches and extending between the second curved segment of the stitch path and the intermediate segment of the stitch path disposed over the strut that extends between the first and second curved crowns of the pair of opposing curved crowns, and wherein widths of the stitches that define the first and second transition zones gradually taper from the width of the stitches that define the first and second curved segment, respectively, to the width of the stitches that define the intermediate segment disposed over the strut that extends between the first and second curved crowns of the pair of opposing curved crowns, and wherein the stent-graft prosthesis has a compressed configuration for delivery within a vasculature and an expanded configuration for deployment within a body lumen.

2. The stent-graft prosthesis of claim 1, wherein a width of the stitches that define each of the remaining curved segments of the stitch path disposed over each of the remaining curved crowns of the plurality of curved crowns of the stent is greater than a width of the respective curved crown of the remaining curved crowns of the stent.

3. The stent-graft prosthesis of claim 1, wherein the tubular graft is a synthetic fabric material.

4. A stent-graft prosthesis comprising:

a tubular graft defining a lumen there-through and having a first end and an opposing second end with a body extending there-between;

a stent coupled to the body of the tubular graft, wherein the stent is a ring that includes a plurality of curved crowns and a plurality of struts with each curved crown being formed between a pair of opposing struts such that the pluralities of curved crowns and struts collectively have a sinusoidal shape; and a plurality of stitches for coupling the stent to the body of the tubular graft, the plurality of stitches forming a stitch path that includes a plurality of curved segments defined by stitches of the plurality of stitches and a plurality of intermediate segments defined by stitches of the plurality of stitches, the pluralities of curved segments and intermediate segments collectively having a sinusoidal shape that corresponds to the sinusoidal shape of the pluralities of struts and curved crowns of the stent, wherein a width of the stitches that define the stitch path varies such that a width of the stitches that define each of first and second curved segments of the stitch path that are disposed over respective first and second curved crowns of a pair of opposing curved crowns of the stent is greater than a width of the respective first or second curved crown of the pair of opposing curved crowns and a width of the stitches that define an intermediate segment of the stitch path disposed over a strut of the plurality of struts that extends between the first and second curved crowns of the pair of opposing curved crowns is approximately the same as a width of the strut so as to permit relative longitudinal movement between the pair of opposing curved crowns and the tubular graft and prevent relative circumferential movement between the pair of opposing curved crowns and the tubular graft, and wherein the stitch path includes a first transition zone defined by stitches of the plurality of stitches and extending between the first curved segment of the stitch path and the intermediate segment of the stitch path disposed over the strut that extends between the first and second curved crowns of the pair of opposing curved crowns, and wherein widths of the stitches that define the first transition zone gradually taper from the width of the stitches that define the first curved segment to the width of the stitches that define the intermediate segment disposed over the strut that extends between the first and second curved crowns of the pair of opposing curved crowns, and wherein the stent-graft prosthesis has a compressed configuration for delivery within a vasculature and an expanded configuration for deployment within a body lumen.

5. The stent-graft prosthesis of claim 4, wherein a width of the stitches that define each curved segment of the stitch path disposed over each of the remaining curved crowns of the plurality of curved crowns of the stent is greater than a width of the respective curved crown of the remaining curved crowns of the stent.

6. The stent-graft prosthesis of claim 4, wherein the tubular graft is a synthetic fabric material.

7. The stent-graft prosthesis of claim 4, wherein the stitch path includes a second transition zone defined by stitches of the plurality of stitches and extending between the second curved segment of the stitch path and the intermediate segment of the stitch path disposed over the strut that extends between the first and second curved crowns of the pair of opposing curved crowns, and wherein widths of the stitches that define the second transition zone gradually taper from the width of the stitches that define the second curved segment to the width of the stitches that define the intermediate segment disposed over the strut that extends between the first and second curved crowns of the pair of opposing curved crowns.

8. A stent-graft prosthesis comprising:

a tubular graft defining a lumen there-through and having a first end and an opposing second end with a body extending there-between;

a stent coupled to the body of the tubular graft, wherein the stent includes a plurality of curved crowns and a plurality of struts with each curved crown being formed between a pair of opposing struts such that the pluralities of struts and curved crowns collectively have a sinusoidal shape; and a plurality of stitches for coupling the stent to the body of the tubular graft, wherein first and second sections of stitches of the plurality of stitches are disposed over respective first and second curved crowns of a pair of opposing curved crowns of the stent and a third section of stitches of the plurality of stitches is disposed over a strut of the plurality of struts that extends between the first and second curved crowns of the pair of opposing curved crowns, wherein a width of the stitches of the first and second sections of stitches is greater than a width of the respective first or second curved crown of the pair of opposing curved crowns and a width of the stitches of the third section of stitches is approximately the same as a width of the strut so as to permit relative longitudinal movement between the pair of opposing curved crowns and the tubular graft and prevent relative circumferential movement between the pair of opposing curved crowns and the tubular graft, and wherein at least a first transition section of stitches of the plurality of stitches is disposed between the first and third sections of stitches and wherein a width of the stitches of the first transition section of stitches gradually taper from the width of the stitches of the first section of stitches to the width of the stitches of the third section of stitches, and wherein the stent-graft prosthesis has a compressed configuration for delivery within a vasculature and an expanded configuration for deployment within a body lumen.

9. The stent-graft prosthesis of claim 8, wherein an additional section of stitches of the plurality of stitches is disposed over each of the remaining curved crowns of the plurality of curved crowns of the stent and a width of the stitches of each additional section of stitches is greater than a width of the respective curved crown of the remaining curved crowns of the stent.

10. The stent-graft prosthesis of claim 8, wherein the tubular graft is a synthetic fabric material.

\* \* \* \* \*